(12) United States Patent
Fan

(10) Patent No.: US 10,750,061 B2
(45) Date of Patent: Aug. 18, 2020

(54) ENDOSCOPE HAVING CAMERA MODULE AND LED ON FLEXIBLE PRINTED CIRCUIT

(71) Applicant: OmniVision Technologies, Inc., Santa Clara, CA (US)

(72) Inventor: Chun-Sheng Fan, Hsinchu (TW)

(73) Assignee: OmniVision Technologies, Inc., Santa Clara, CA (US)

( * ) Notice: Subject to any disclaimer, the term of this patent is extended or adjusted under 35 U.S.C. 154(b) by 152 days.

(21) Appl. No.: 15/705,523

(22) Filed: Sep. 15, 2017

(65) Prior Publication Data

US 2019/0089875 A1    Mar. 21, 2019

(51) Int. Cl.
| | |
|---|---|
| *H04N 5/225* | (2006.01) |
| *G02B 23/24* | (2006.01) |
| *F21V 19/00* | (2006.01) |
| *H01L 33/62* | (2010.01) |
| *A61B 1/05* | (2006.01) |
| *A61B 1/005* | (2006.01) |
| *A61B 1/06* | (2006.01) |
| *A61B 1/00* | (2006.01) |
| *F21Y 115/10* | (2016.01) |

(52) U.S. Cl.
CPC ......... *H04N 5/2253* (2013.01); *A61B 1/0011* (2013.01); *A61B 1/0055* (2013.01); *A61B 1/051* (2013.01); *A61B 1/0676* (2013.01); *A61B 1/0684* (2013.01); *F21V 19/0015* (2013.01); *G02B 23/2461* (2013.01); *G02B 23/2484* (2013.01); *H01L 33/62* (2013.01); *H04N 5/2257* (2013.01); *F21Y 2115/10* (2016.08); *H04N 2005/2255* (2013.01)

(58) Field of Classification Search
CPC ........................... H04N 5/2253; A61B 1/0011
See application file for complete search history.

(56) References Cited

U.S. PATENT DOCUMENTS

| | | | |
|---|---|---|---|
| 2008/0207996 A1 | 8/2008 | Tsai | |
| 2012/0140101 A1* | 6/2012 | Afshari | H04N 5/2257 348/308 |
| 2015/0292722 A1* | 10/2015 | Uehara | H05K 1/0277 362/382 |
| 2017/0105605 A1 | 4/2017 | Hebert | |
| 2017/0224203 A1* | 8/2017 | Tanahashi | A61B 1/04 |

* cited by examiner

*Primary Examiner* — William C Vaughn, Jr.
*Assistant Examiner* — Jerry T Jean Baptiste

(57) ABSTRACT

An endoscope comprises a FPC (flexible printed circuit) having a first side and a second side, where the FPC comprises a first head part, a body part, and tail part. At least one solder pad is on the first side of the first head part, and at least one solder pad is on the first side of the body part. The endoscope further comprises a camera module mounted on the first side of the body part and a first LED (light emitting diode). A first side of the first LED is mounted on the first side of the first head part and a second side of the first LED is mounted on a first side of the camera module, while the first head part is bent. The second side of the body part is mounted on an end of a flexible fiber, and the tail part of the FPC is bent to mount on the flexible fiber.

20 Claims, 5 Drawing Sheets

ENDOSCOPE HAVING CAMERA MODULE AND LED ON FLEXIBLE PRINTED CIRCUIT

FIELD OF THE INVENTION

This invention relates to an endoscope, and more specifically relates to an endoscope having camera module and LED on flexible printed circuit.

BACKGROUND OF THE INVENTION

An endoscope is a medical diagnostic instrument used for imaging a ventricle within a patient. It includes a flexible shaft capable of being inserted into the patient through an orifice thereof. The shaft has a tip that includes a light source and a camera for respectively illuminating and capturing images of part of the patient, such as a body cavity or an organ.

An endoscope includes at least a camera for capturing an image or video and a LED for illuminating otherwise dark space inside human body. A smaller endoscope would cause a smaller incision and reduce patient's suffering. Accordingly, low cost endoscopes having small cross-sections which cause minimum incisions are demanded.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

FIG. 7 schematically illustrates the second side of the body part of the FPC mounted on the end of the flexible fiber, and the tail part of the FPC bent toward flexible fiber according to an embodiment of the present invention.

Figure 1:
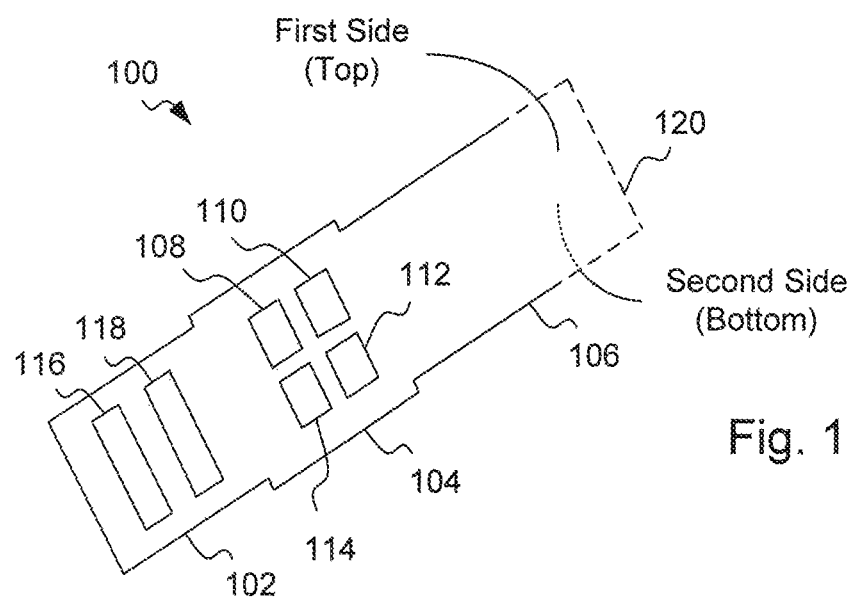
FIG. 1 schematically illustrates a FPC (flexible printed circuit) comprising a first head part, a body part, and a tail part, according to an embodiment of the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exagerated relative to other elements to help to improve understanding of various embodiments of the present invention.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable combinations and/or sub-combinations in one or more embodiments.

FIG. 1 schematically illustrates a FPC (flexible printed circuit) 100 comprising a first head part 102, a body part 104, and a tail part 106, according to an embodiment of the present invention. First head part 102, body part 104, and tail part 106 may be made of the same material and having the same structure, or made of different materials and having different structures. First head part 102 can be bent from body part 104. Similarly, tail part 106 can be bent from body part 104. The widths of first head part 102, body part 104, and tail part 106 may be the same or different. Tail part 106 may be narrower than first head part 102 and body part 104.

FPC 100 comprises a first side and a second side. A solder pad or a plurality of solder pads may be disposed on the first side of body part 104 of FPC 100. For example, solder pads 108, 110, 112, and 114 are disposed on the first side of body part 104. It is appreciated, different numbers and sizes of solders pads on body part 104 are possible.

A solder pad or a plurality of solder pads may be disposed on the first side of first head part 102 of FPC 100. For example, solder pads 116 and 118 are disposed on the first side of first head part 102. It is appreciated, different numbers and sizes of solders pads on first head part 102 are possible.

Tail part 106 may be longer than first head part 102. Solder pads on the first side of first head part 102 and the first side of body part 104 may be electrically connected to wires on FPC 100, and may be electrically coupled to an end 120 of tail part 106. The wires may be on the second side of FPC 100 or the first side of FPC 100. In an embodiment, the wires may be inside FPC 100.

Figure 2:
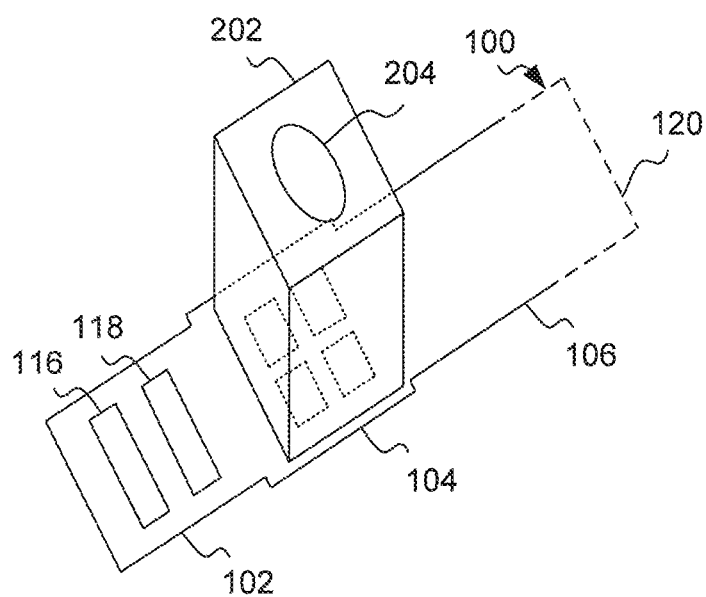
FIG. 2 schematically illustrates a camera module disposed on the first side of the body part of the FPC according to an embodiment of the present invention.

FIG. 2 schematically illustrates a camera module 202 disposed on the first side of body part 104 of FPC 100, according to an embodiment of the present invention. Camera module 202 may be a small size camera module. For example, camera module 202 may have dimension of 1 mm×1 mm×2.4 mm. A cross-section of camera module 202 may be less than 2 mm×2 mm. Camera module 202 may have an aperture 204 to allow incident light to form an image on an image sensor of camera module 202. An imaging lens (not shown) may form the image on the image sensor (not shown) in camera module 202. Camera module 202 may be in a CSP (chip scale package) having solder balls or bumps. For example, a bottom of camera module 202 includes four solder balls or electrodes. The four solder balls or electrodes are reflowed or soldered to solder pads 108, 110, 112, and 114 on the first side of body part 104. The solder balls are reflowed to attach to the solder pad or the plurality of solder pads on the first side of body part 104 of FPC 100. Camera module 202 is operating by properly coupling its solder balls or electrodes to an appropriate device (not shown).

The size of body part 104 may be same as, smaller than, or larger than camera module 202. In an embodiment, body part 104 may be a little larger than camera module 202. For example, for camera module having cross-section 1 mm×1 mm, the size of body part 104 may be in the proximity of 1.3 mm×1.3 mm. It is appreciated that body part 104 may be a square, rectangle, circle, ellipse, or of any shape.

Figure 3:
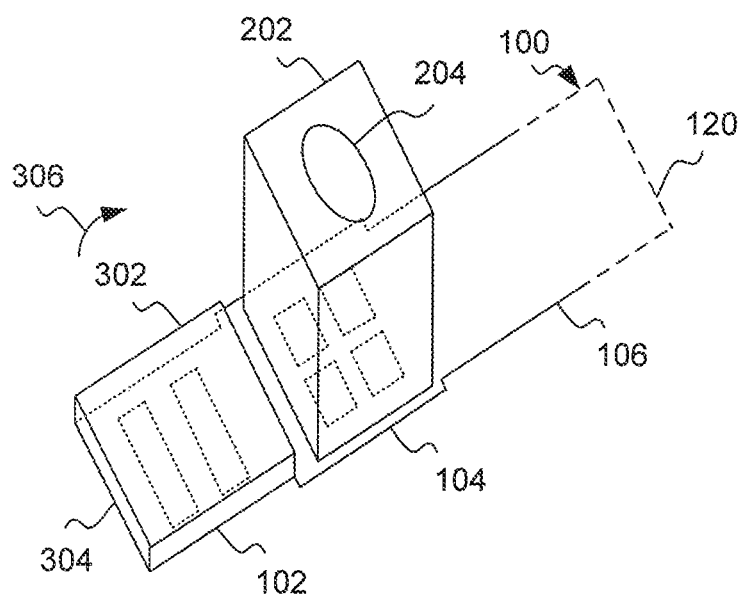
FIG. 3 schematically illustrates a first LED (light emitting diode) disposed on the first side of the first head part of the FPC according to an embodiment of the present invention.

FIG. 3 schematically illustrates a first LED (light emitting diode) 302 disposed on the first side of first head part 102 of FPC 100, according to an embodiment of the present invention. First LED 302 may be a small size LED. For example, first LED 302 may have dimension of 1 mm×2.4 mm×0.3 mm. A cross-section of first LED 302 may be less than 2 mm×0.6 mm. First LED 302 may have an end 304 for emitting light. For example, first LED 302 has two solder balls or electrodes. The two solder balls or electrodes are reflowed or soldered to solder pads 116 and 118 on the first side of first head part 102. In an embodiment, a first side of first LED 302, for example, the side having dimension 1 mm×2.4 mm and having solder balls or electrodes, is mounted on the first side of first head part 102 by reflowing or soldering its solder balls or electrodes to solder pads 116 and 118. The solder balls or electrodes are reflowed to attach to the solder pad or the plurality of solder pads on the first side of first head part 102 of FPC 100. In an embodiment, additional glue may be used to glue the first side of first LED 302 to the first side of first head part 102. After the first side of first LED 302 is mounted on the first side of first head part 102, first head part 102 is bent along a direction 306. The first side of first head part 102 is bent toward body part 104.

Figure 4:
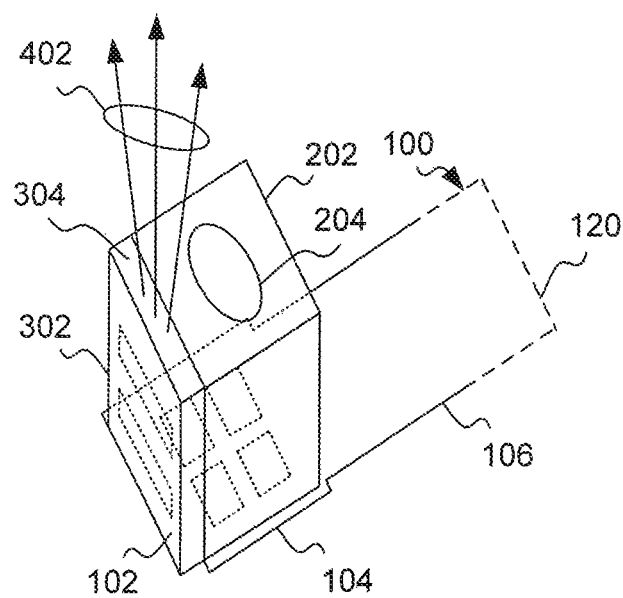
FIG. 4 schematically illustrates the first side of the first head part bent toward the camera module according to an embodiment of the present invention.

FIG. 4 schematically illustrate that the first side of first head part 102 is bent toward camera module 202, according to an embodiment of the present invention. A second side of first LED 302 is abutted against a first side of camera module 202. The second side of first LED 302 may be mounted on the first side of camera module 202 using glue. First LED 302 is operating by properly coupling its solder balls or electrodes to an appropriate device (not shown). First LED 302 may emit light 402 from end 304 when it is turned on.

Figure 5:
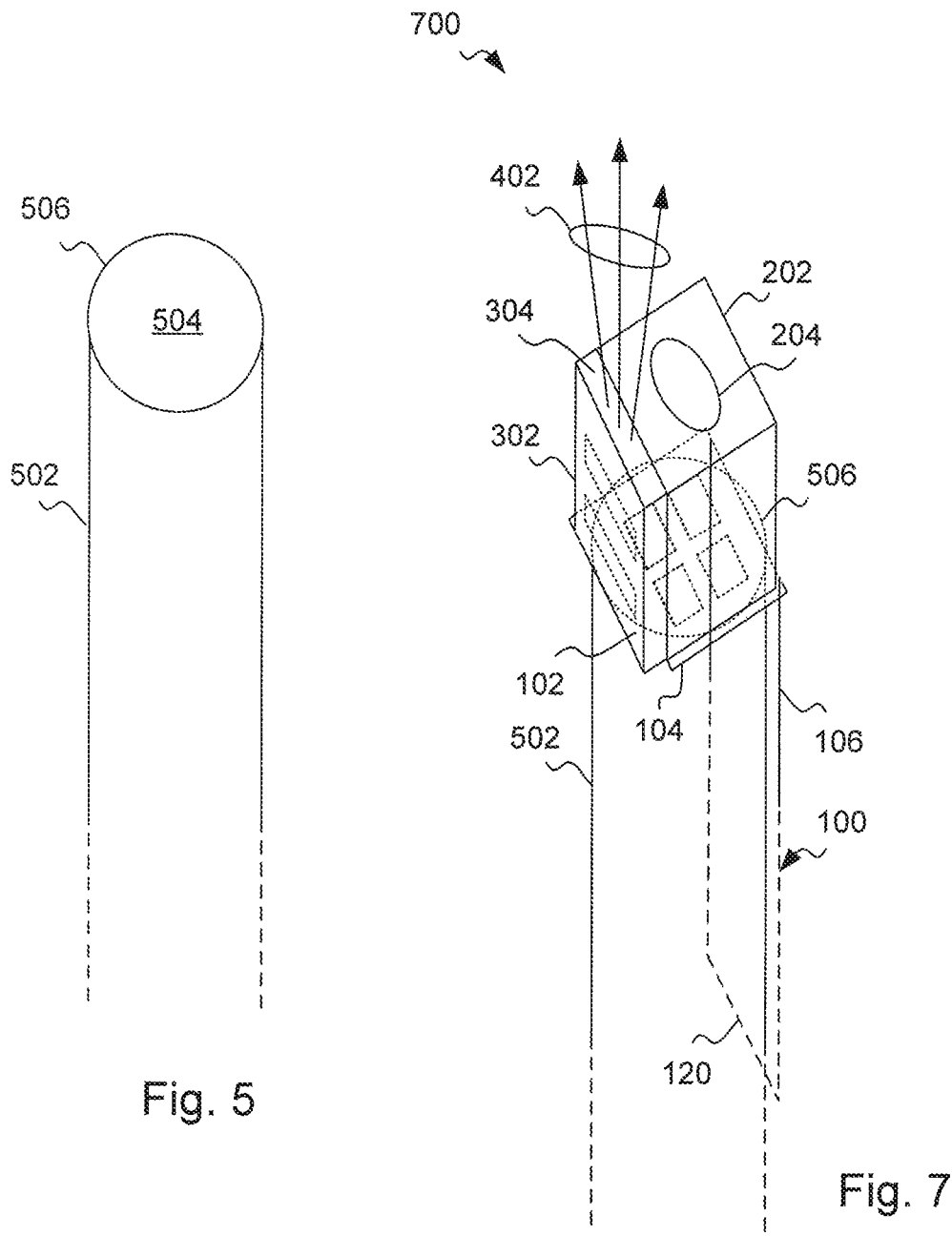
FIG. 5 schematically illustrates a flexible fiber having an end and a cross-section according to an embodiment of the present invention.

FIG. 5 schematically illustrates a flexible fiber 502 having an end 506 and a cross-section 504, according to an embodiment of the present invention. Flexible fiber 502 may be a silica fiber, PMMA (polymethyl methacrylate) fiber, PTFE (polytetrafluoroethylene) fiber, or the like.

Figure 6:
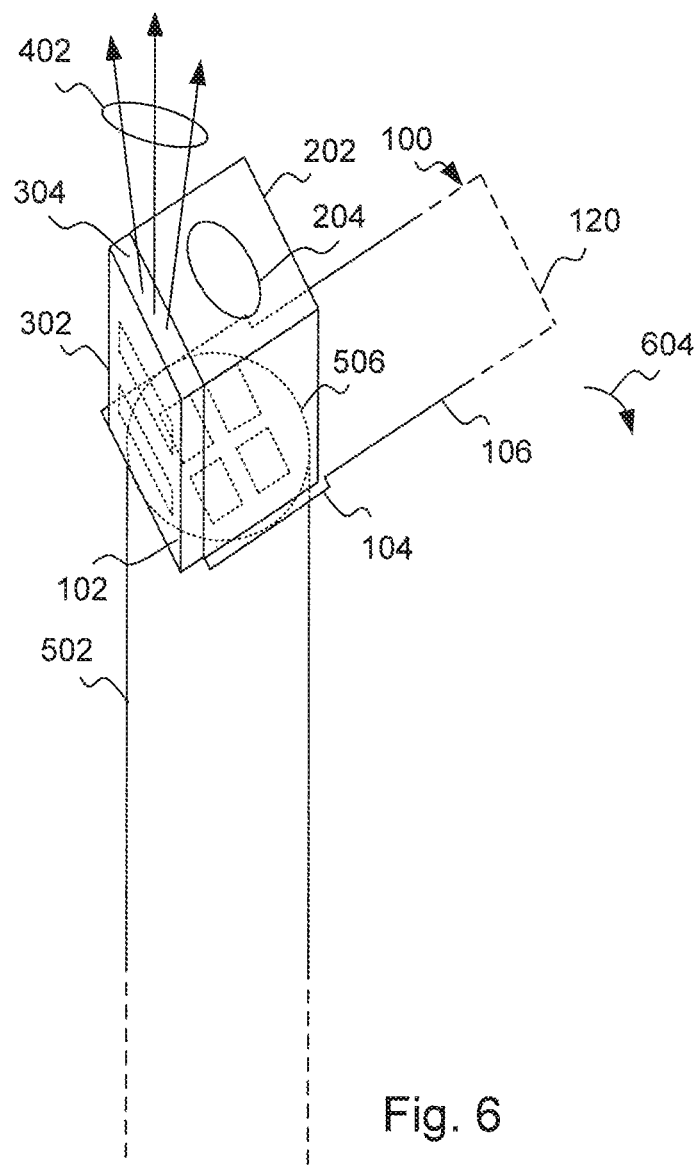
FIG. 6 schematically illustrates the body part of the FPC disposed on the end of the flexible fiber according to an embodiment of the present invention.

FIG. 6 schematically illustrates that body part 104 of FPC 100 is disposed on end 506 of flexible fiber 502, according to an embodiment of the present invention. First LED 302 is mounted on camera module 202. In this manner, the second side of body part 104 of FPC 100 attaches to end 506 of flexible fiber 502, and the first side of body part 104 of FPC 100 attaches to camera module 302. The second side of body part 104 of FPC 100 may be attached to end 506 of flexible fiber 502 using glue or other means including thermal fusion bonding and the like. After the second side of body part 104 of FPC 100 is mounted on end 506 of flexible fiber 502, tail part 106 of FPC 100 is bent along a direction 604. The second side of tail part 106 is bent toward body part 104.

Cross-section 504 (see FIG. 5) of flexible fiber 502 may be same as, smaller than, or larger than body part 104 of FPC 100. In an embodiment, body part 104 may be about the same as cross-section 504. For example, for camera module having cross-section 1 mm×1 mm and the size of body part 104 in the proximity of 1.3 mm×1.3 mm, cross-section 504 may be a circle of 1.3 mm diameter. The diameter of the cross-section of the flexible fiber may be less than 2.6 mm. It is appreciated that cross-section 504 is not limited to circle. A flexible fiber having any shape of cross-section may be used as well.

FIG. 7 schematically illustrates that the second side of body part 104 of FPC 100 is mounted on end 506 of flexible fiber 502, and tail part 106 of FPC 100 is bent toward flexible fiber 502, according to an embodiment of the present invention. Tail part 106 is bent to abut flexible fiber 502. The second side of tail part 106 of FPC 100 may be mounted on flexible fiber 502 using glue or other means including thermal fusion bonding and the like. In this manner, first LED 302 is mounted on the first side of camera module 202 and camera module 202 is mounted on FPC 100 as an integrated part, and the integrated part is on end 506 of flexible fiber 502 forming an endoscope 700, according to an embodiment of the present invention. Endoscope 700 has a cross-section as small as the combined cross-section of camera module 202 and LED 302. For example, the combined cross-section may be 1 mm×1.03 mm.

Endoscope 700 may include additional transparent or partially transparent housing. Endoscope 700 may be included in a more complex endoscope unit having additional functions such as equipment for biopsy. In an embodiment, endoscope 700 as illustrated in FIG. 7 may be adequate for use to take pictures or video inside human body. It is understood that endoscope 700 is electrically coupled to an appropriate device (not shown). When endoscope 700 is inside human body, first LED 302 emits light 402 from end 304, light 402 illuminates an object inside human body, and camera module 202 captures a picture or a video of the object illuminated by light 402, which may be displayed using an external display (not shown) coupled to endoscope 700.

Figure 8:
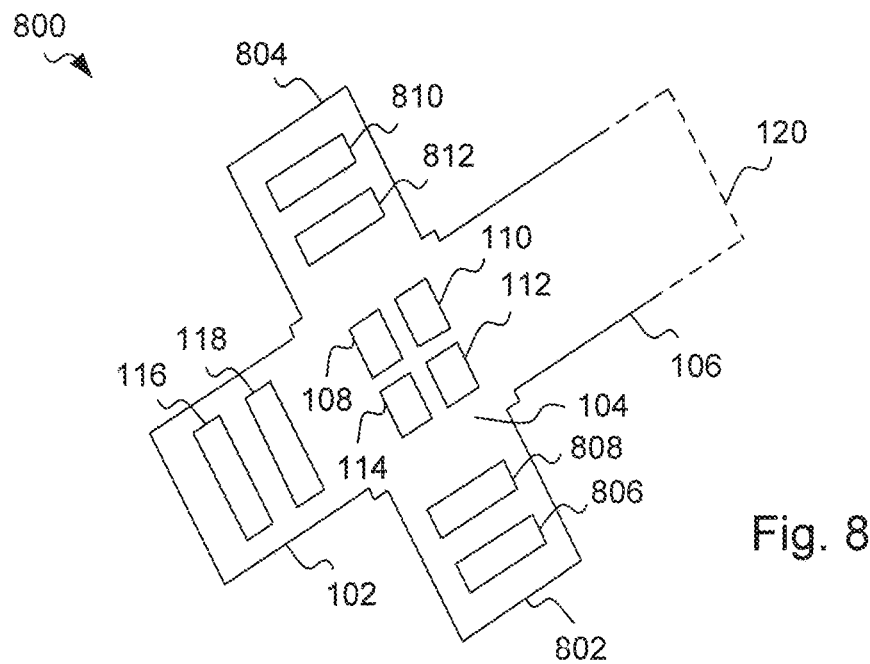
FIG. 8 schematically illustrates a FPC comprising a first head part, a second head part, a third head part, a body part, and a tail part, according to an embodiment of the present invention.

FIG. 8 schematically illustrates a FPC 800 comprising a first head part 102, a second head part 802, a third head part 804, a body part 104, and a tail part 106, according to an embodiment of the present invention. FPC 800 is similar to FPC 100 of FIG. 1, except FPC 800 further comprises additional second head part 802 and third head part 804. First head part 102, second head part 802, and third head part 804 can be bent from body part 104. Similarly, tail part 106 can be bent from body part 104. The widths of first head part 102, second head part 802, third head part 804, body part 104, and tail part 106 may be the same or different. Tail part 106 may be narrower than other parts.

A solder pad or a plurality of solder pads may also be disposed on the first side of second head part 802 and the first side of third head part 804 of FPC 800. For example, solder pads 806 and 808 are disposed on the first side of second head part 802, and solder pads 810 and 812 are disposed on the first side of third head part 804. It is appreciated, different numbers and sizes of solders pads on second head part 802 and third head part 804 are possible.

Tail part 106 may be longer than first head part 102, second head part 802, or third head part 804. Solder pads on the first side of first head part 102, second head part 802, third head part 804, and body part 104 may be electrically connected to wires on FPC 800, and may be electrically coupled to an end 120 of tail part 106. The wires may be on the second side of FPC 800 or the first side of FPC 800. In an embodiment, the wires may be inside FPC 800.

In this manner, three LEDs may be disposed on the first side of first head part 102, the first side of second head part 802, and the first side of third head part 804, respectively. The three LEDs may be mounted onto the camera module disposed on the first side of body part 104 of FPC 800.

Figure 9:
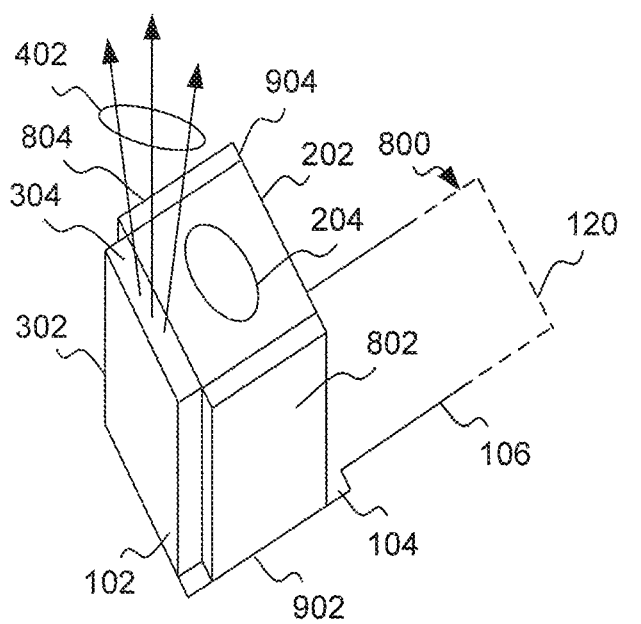
FIG. 9 schematically illustrates an endoscope having three LEDs, according to an embodiment of the present invention.

FIG. 9 schematically illustrates an endoscope having three LEDs, according to an embodiment of the present invention. The first side of first LED 302 is mounted on the first side of first head part 102, and the second side of first LED 302 is mounted on the first side of camera module 202, while first head part 102 is bent. A first side of a second LED 902 is mounted on the first side of second head part 802, and a second side of second LED 902 is mounted on a second side of camera module 202, while second head part 802 is bent. A first side of a third LED 904 is mounted on the first side of third head part 804, and a second side of third LED 904 is mounted on a third side of camera module 202, while third head part 804 is bent. The three LEDs may illuminate the body cavity. The embodiment illustrated in FIG. 9 may be disposed on end 506 of flexible fiber 502 as shown in FIG. 6.

It is appreciated that, in an embodiment, FPC 800 has only two head parts, and only two LEDs are mounted on camera module 202 disposed on the first side of body part 104 of FPC 800. In this embodiment, two LEDs may illuminate the body cavity.

While the present invention has been described herein with respect to the exemplary embodiments and the best mode for practicing the invention, it will be apparent to one of ordinary skill in the art that many modifications, improvements and sub-combinations of the various embodiments, adaptations and variations can be made to the invention without departing from the spirit and scope thereof.

The terms used in the following claims should not be construed to limit the invention to the specific embodiments disclosed in the specification and the claims. Rather, the scope is to be determined entirely by the following claims, which are to be construed in accordance with established doctrines of claim interpretation. The present specification and figures are accordingly to be regarded as illustrative rather than restrictive.

What is claimed is:

1. An endoscope comprising:
   a FPC (flexible printed circuit) having a first side and a second side, the FPC comprising a first head part, a body part, and a tail part;
   wherein at least one solder pad is on the first side of the first head part, and at least one solder pad is on the first side of the body part;
   a camera module mounted on the first side of the body part;
   a first LED (light emitting diode), wherein a first side of the first LED is mounted on the first side of the first head part, and a second side of the first LED is mounted on a first side of the camera module; and
   wherein the first head part is bent toward the camera module.

2. The endoscope of claim 1, wherein the second side of the body part is mounted on an end of a flexible fiber, and the tail part of the FPC is bent to abut the flexible fiber.

3. The endoscope of claim 2, wherein the bent tail part of the FPC is mounted on the flexible fiber.

4. The endoscope of claim 1, wherein the camera module includes solder balls.

5. The endoscope of claim 4, wherein the camera module is in a CSP (chip scale package).

6. The endoscope of claim 4, wherein the solder balls of the camera module are reflowed to attach to the at least one solder pad on the first side of the body part.

7. The endoscope of claim 1, wherein the first LED includes one of a solder ball and an electrode, and wherein the one of a solder ball and an electrode of the first LED is reflowed to attach to the at least one solder pad on the first side of the first head part.

8. The endoscope of claim 1, wherein a cross-section of the camera module is less than 2 mm×2 mm.

9. The endoscope of claim 1, wherein a cross-section of the first LED module is less than 2 mm×0.6 mm.

10. The endoscope of claim 1, wherein the flexible fiber has a circular cross-section.

11. The endoscope of claim 10, wherein the diameter of the cross-section of the flexible fiber is less than 2.6 mm.

12. The endoscope of claim 1, wherein the FPC having the first side and the second side further comprises a second head part.

13. The endoscope of claim 12 further comprising:
   a second LED, wherein a first side of the second LED is mounted on the first side of the second head part, and a second side of the second LED is mounted on a second side of the camera module; and
   wherein the second head part is bent.

14. The endoscope of claim 13, wherein the FPC having the first side and the second side further comprises a third head part.

15. The endoscope of claim 14 further comprising:
   a third LED, wherein a first side of the third LED is mounted on the first side of the third head part, and a second side of the third LED is mounted on a third side of the camera module; and
   wherein the third head part is bent.

16. A method for manufacturing an endoscope comprising:
   providing a FPC (flexible printed circuit) having a first side and a second side, the FPC comprising a first head part, a body part, and a tail part;
   mounting a camera module on the first side of the body part;
   mounting a first side of a first LED (light emitting diode) on the first side of the first head part;
   bending the first head part toward the camera module; and
   mounting a second side of the first LED on a first side of the camera module.

17. The method of claim 16 further comprising:
   mounting the second side of the body part on an end of a flexible fiber; and
   bending the tail part of the FPC toward the flexible fiber.

18. The method of claim 17 further comprising:
   mounting the bent tail part of the FPC on the flexible fiber.

19. The method of claim 16 wherein the FPC further comprises a second head part, and the method further comprising:
   mounting a first side of a second LED on the first side of the second head part;
   bending the second head part toward the camera module; and
   mounting a second side of the second LED on a second side of the camera module.

20. The method of claim 19 wherein the FPC further comprises a third head part, and the method further comprising:
   mounting a first side of a third LED on the first side of the third head part;

bending the third head part toward the camera module; and mounting a second side of the third LED on a third side of the camera module.

* * * * *